(12) United States Patent
Rother et al.

(10) Patent No.: US 10,006,061 B2
(45) Date of Patent: Jun. 26, 2018

(54) LYASE AND LYASE-ENCODING DNA, VECTORS CONTAINING THE DNA, AND METHOD FOR THE ASYMMETRIC SYNTHESIS OF (S)-PHENYLACETYLCARBINOL

(71) Applicant: Forschungszentrum Juelich GmbH, Juelich (DE)

(72) Inventors: Doerte Rother, Huerth (DE); Martina Pohl, Aachen (DE); Torsten Sehl, Offenburg (DE); Lisa Marx, Seeheim-Jugenheim (DE); Robert Westphal, Leipzig (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days. days.

(21) Appl. No.: 15/511,317

(22) PCT Filed: Aug. 14, 2015

(86) PCT No.: PCT/DE2015/000407
§ 371 (c)(1),
(2) Date: Mar. 15, 2017

(87) PCT Pub. No.: WO2016/041533
PCT Pub. Date: Mar. 24, 2016

(65) Prior Publication Data
US 2017/0253894 A1    Sep. 7, 2017

(30) Foreign Application Priority Data
Sep. 16, 2014 (DE) .................. 10 2014 013 644

(51) Int. Cl.
| | |
|---|---|
| *C12P 7/40* | (2006.01) |
| *C12P 7/02* | (2006.01) |
| *C12N 1/20* | (2006.01) |
| *C12N 9/88* | (2006.01) |
| *C12P 7/26* | (2006.01) |
| *C12N 9/04* | (2006.01) |
| *C12P 7/42* | (2006.01) |

(52) U.S. Cl.
CPC ............... *C12P 7/26* (2013.01); *C12N 9/88* (2013.01); *C12N 9/0006* (2013.01); *C12P 7/42* (2013.01); *C12Y 401/01001* (2013.01)

(58) Field of Classification Search
CPC .... C12Y 401/01001; C12Y 101/01001; C12N 9/88; C12N 9/008; C12N 15/74; C12P 7/18
USPC ........... 435/252.3, 320.1, 136, 146; 536/23.2
See application file for complete search history.

(56) References Cited

U.S. PATENT DOCUMENTS

| | | |
|---|---|---|
| 5,789,166 A | 8/1998 | Bauer et al. |
| 5,932,419 A | 8/1999 | Bauer et al. |
| 6,391,548 B1 | 5/2002 | Bauer et al. |
| 2013/0309732 A1 | 11/2013 | Kao Chao-Hung et al. |

FOREIGN PATENT DOCUMENTS

WO    WO 2010039750 A2    4/2010

OTHER PUBLICATIONS

Doerte Rother, et al., "S-Selective Mixed Carboligation by Structure-Based Design of the Pyruvate Decarboxylase from Acetobacter pasteurianus", ChemCatChem vol. 3, No. 10, Dec. 2011, pp. 1587-1596.
Robert Westphal, et al., A Tailor-Made Chimeric Thiamine Diphosphate Dependent Enzyme for the Direct Asymmetric Synthesis of (S)-Benzoins, Angewandte Chemie, vol. 53, issue 35, Aug. 25, 2014, pp. 9376-9379.
D. Gocke, et al., "Rationales Enzymdesign für die (S)-selektive Benzoinkondensation", Chemie Ingenieur Technik vol. 81, No. 8, Dec. 2009, p. 1256.
Doerte Gocke, et al., "Rational Protein Design of ThDP-Dependent Enzymes: Engineering Stereoselectivity", ChemBioChem vol. 9, issue 3, Feb. 15, 2008, pp. 107-115.
Waldemar, et al., "Synthesis of Optically Active a-Hydroxy Carbonyl Compounds by the Catalytic, Enantioselective Oxidation of Silyl Enol Ethers and Ketene Acetals with (Salen)manganese(III) Complexes", J. Am. Chem. Soc., 1998, 120 (4), pp. 708-714, Jan. 16, 1998.
J. Brussee, et al., "Bio-Organic Synthesis of Optically Active Cyanohydrins and Acyloins", Tetrahedron Letters, vol. 29, No. 35, pp. 4485-4488, Dec. 1988.
Franklin A. Davis, et al., Influence of Enolate Geometry and Structure on the Stereochemistry of the Asymmetric Oxidation of Prochiral Ketone Ensolates to Optically Active a-Hydroxy Ketones, Tetrahedron Letters, vol. 30, No. 7, pp. 779-782, Dec. 1989.
Doerte Rother, et al., "S-Selective Mixed Carboligation by Structure-Based Design of the Pyruvate Decarboxylase from Acetobacter pasteurianus", ChemCatChem vol. 3, Dec. 2011, pp. 1587-1596.
Steven A. Fleming, et al., "Asymmetric dihydroxylation of allenes", Tetrahedron Letters vol. 45, issue 17, Apr. 19, 2004, pp. 3341-3343.
Manfred T. Reetz, et al., "Addressing the Numbers Problem in Directed Evolution", ChemBioChem vol. 9, Dec. 2008, pp. 1797-1804.
Esa Toukoniitty, et al., "Enantioselective Hydrogenation of 1-Phenyl-1, 2-propanedione", Journal of Catalysis vol. 204, Dec. 2001, pp. 281-291.

(Continued)

*Primary Examiner* — Tekchand Saidha
*Assistant Examiner* — Mohammad Y Meah
(74) *Attorney, Agent, or Firm* — Leydig, Voit & Mayer, Ltd.

(57) ABSTRACT

The invention relates to a lyase and a lyase-encoding DNA, to vectors containing the DNA and to a method for the asymmetric synthesis of (S)-phenylacetylcarbinol. According to the invention, a lyase is provided, in which tryptophan is replaced with an amino acid at position 543 in protein ApPDC-E469G, said protein being modified with respect to the wild type of *Aceobacter pasteurianus*, or in which it is less space-filling than tryptophan. According to the invention, deoxyribonucleic acids are furthermore provided, which encode the lyase. (S)-phenylacetylcarbinol can be produced with the lyase according to the invention from the educts benzaldehyde and pyruvate or acetaldehyde with an enantiomeric excess of at least 94%.

7 Claims, 1 Drawing Sheet

(56) References Cited

OTHER PUBLICATIONS

Waldemar Adam, et al., "Asymmetric C—H Oxidation of vic-Diols to a-Hydroxy Ketones by a Fructose-Derived Dioxirane: Electronic Effects on the Enantioselectivity of Oxygen Transfer", J. Org. Chem. vol. 64, Dec. 1999, pp. 7492-7497.

Zi-Qiang Rong, et al., "Enantioselective Oxidation of 1, 2-Diols with Quinine-Derived Urea Organocatalyst", Organic Letters, vol. 16, No. 1, Dec. 2014, pp. 208-2011.

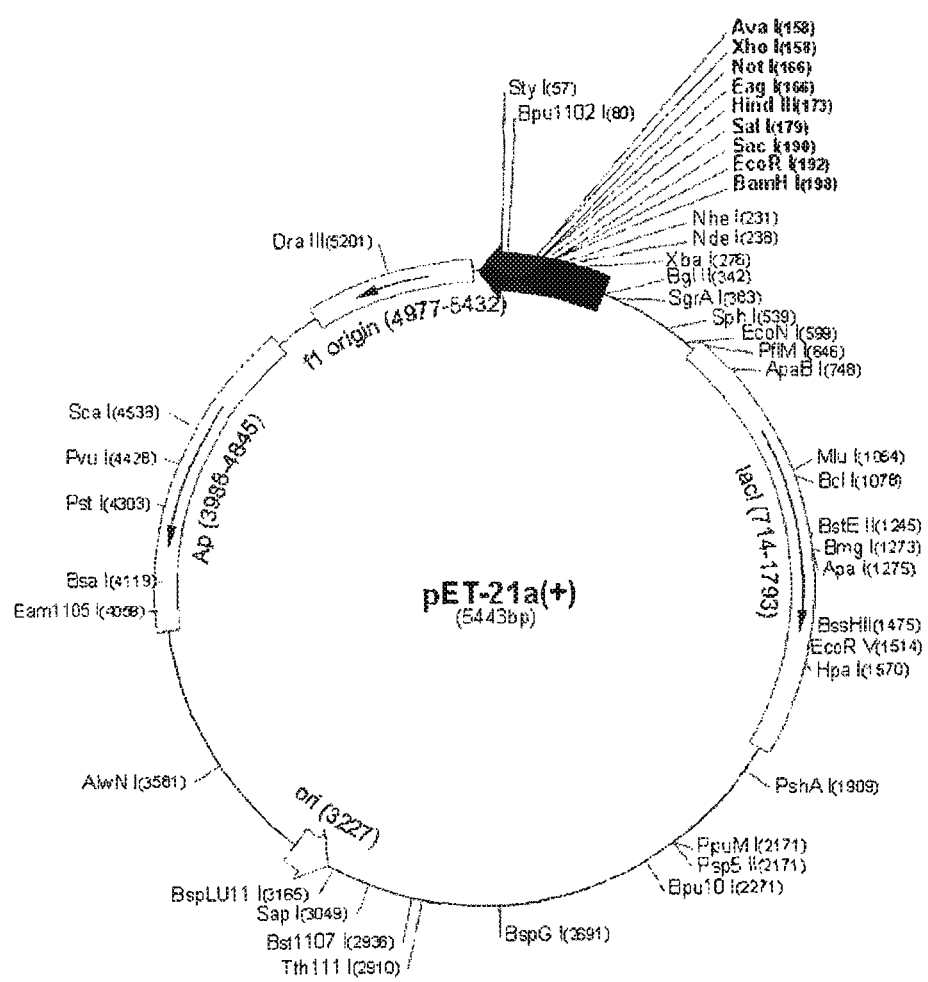

SEQUENCE LISTING

```
<160> NUMBER OF SEQ ID NOS: 31

<210> SEQ ID NO 1
<211> LENGTH: 560
<212> TYPE: PRT
<213> ORGANISM: Artificial Sequence
<220> FEATURE:
<223> OTHER INFORMATION: Synthetic

<400> SEQUENCE: 1

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
```

```
                225                 230                 235                 240
            Thr Ile Met Ala Ala Ala Lys Gly Phe Phe Pro Glu Asp His Ala Gly
                            245                 250                 255
            Phe Arg Gly Leu Tyr Trp Gly Glu Val Ser Asn Pro Gly Val Gln Glu
                            260                 265                 270
            Leu Val Glu Thr Ser Asp Ala Leu Leu Cys Ile Ala Pro Val Phe Asn
                            275                 280                 285
            Asp Tyr Ser Thr Val Gly Trp Ser Ala Trp Pro Lys Gly Pro Asn Val
                            290                 295                 300
            Ile Leu Ala Glu Pro Asp Arg Val Thr Val Asp Gly Arg Ala Tyr Asp
            305                 310                 315                 320
            Gly Phe Thr Leu Arg Ala Phe Leu Gln Ala Leu Ala Glu Lys Ala Pro
                            325                 330                 335
            Ala Arg Pro Ala Ser Ala Gln Lys Ser Ser Val Pro Thr Cys Ser Leu
                            340                 345                 350
            Thr Ala Thr Ser Asp Glu Ala Gly Leu Thr Asn Asp Glu Ile Val Arg
                            355                 360                 365
            His Ile Asn Ala Leu Leu Thr Ser Asn Thr Thr Leu Val Ala Glu Thr
                            370                 375                 380
            Gly Asp Ser Trp Phe Asn Ala Met Arg Met Thr Leu Pro Arg Gly Ala
            385                 390                 395                 400
            Arg Val Glu Leu Glu Met Gln Trp Gly His Ile Gly Trp Ser Val Pro
                            405                 410                 415
            Ser Ala Phe Gly Asn Ala Met Gly Ser Gln Asp Arg Gln His Val Val
                            420                 425                 430
            Met Val Gly Asp Gly Ser Phe Gln Leu Thr Ala Gln Glu Val Ala Gln
                            435                 440                 445
            Met Val Arg Tyr Glu Leu Pro Val Ile Phe Leu Ile Asn Asn Arg
                            450                 455                 460
            Gly Tyr Val Ile Gly Ile Ala Ile His Asp Gly Pro Tyr Asn Tyr Ile
            465                 470                 475                 480
            Lys Asn Trp Asp Tyr Ala Gly Leu Met Glu Val Phe Asn Ala Gly Glu
                            485                 490                 495
            Gly His Gly Leu Gly Leu Lys Ala Thr Thr Pro Lys Glu Leu Thr Glu
                            500                 505                 510
            Ala Ile Ala Arg Ala Lys Ala Asn Thr Arg Gly Pro Thr Leu Ile Glu
                            515                 520                 525
            Cys Gln Ile Asp Arg Thr Asp Cys Thr Asp Met Leu Val Gln His Gly
                            530                 535                 540
            Arg Lys Val Ala Ser Thr Asn Ala Arg Lys Thr Thr Leu Ala Leu Glu
            545                 550                 555                 560

<210> SEQ ID NO 2
<211> LENGTH: 1680
<212> TYPE: DNA
<213> ORGANISM: Artificial Sequence
<220> FEATURE:
<223> OTHER INFORMATION: Synthetic

<400> SEQUENCE: 2
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acgggctgc ggcagcggtt gtcaccttca gcgttggcgc catttccgcc      240
```

```
atgaacgccc tcggcggcgc ctatgccgaa aacctgccgg ttatcctgat ttccggcgcg      300
cccaacagca atgatcaggg cacaggtcat atcctgcatc acacaatcgg caagacggat      360
tacagctacc agcttgaaat ggcccgtcag gtcacctgtg ccgccgaaag cattaccgac      420
gctcactccg ccccggccaa gattgaccac gtcattcgca cggcgctgcg cgagcgtaag      480
ccggcctatc tggacatcgc gtgcaacatt gcctccgagc cctgcgtgcg gcctggccct      540
gtcagcagcc tgctgtccga gcctgaaatc gaccacacga gcctgaaggc cgcagtggac      600
gccacggttg ccttgctgga aaaatcggcc agccccgtca tgctgctggg cagcaagctg      660
cgggccgcca acgcactggc cgcaaccgaa acgctggcag acaagctgca atgcgcggtg      720
accatcatgg cggccgcgaa aggcttttc cccgaagacc acgcgggttt ccgcggcctg      780
tactggggcg aagtctcgaa ccccggcgtg caggaactgg tggagacctc cgacgcactg      840
ctgtgcatcg cccccgtatt caacgactat tcaacagtcg gctggtcggc atggcccaag      900 ggcccccaatg tgattctggc tgagcccgac cgcgtaacgg tcgatggccg cgcctatgac      960
ggctttaccc tgcgcgcctt cctgcaggct ctggcggaaa agcccccgc gcgcccggcc     1020 tccgcacaga aaagcagcgt cccgacgtgc tcgctcaccg cgacatccga tgaagccggt     1080
ctgacgaatg acgaaatcgt ccgtcatatc aacgccctgc tgacatcaaa cacgacgctg     1140
gtggcagaaa ccggcgattc atggttcaat gccatgcgca tgaccctgcc gcgcggtgcg     1200
cgcgtggaac tggaaatgca gtggggccat atcggctggt ccgtgccctc cgccttcggc     1260
aatgccatgg gctcgcagga ccgccagcat gtggtgatgg taggcgatgg ctccttccag     1320
cttaccgcgc aggaagtggc tcagatggtg cgctacgaac tgcccgtcat tatctttctg     1380
atcaacaacc gtggctatgt cattggcatc gccattcatg acggcccgta caactatatc     1440
aagaactggg attacgccgg cctgatggaa gtcttcaacg ccggagaagg ccatggactt     1500
ggcctgaaag ccaccacccc gaaggaactg acagaagcca tcgccagggc aaaagccaat     1560
acccgcggcc cgacgctgat cgaatgccag atcgaccgca cggactgcac ggatatgctg     1620
gttcaacatg ccgcaaggt tgcctcaacc aacgcgcgca agaccactct ggccctcgag     1680
```

<210> SEQ ID NO 3
<211> LENGTH: 560
<212> TYPE: PRT
<213> ORGANISM: Artificial Sequence
<220> FEATURE:
<223> OTHER INFORMATION: Synthetic

<400> SEQUENCE: 3

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110
```

-continued

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
            195                 200                 205

Ser Ala Ser Pro Val Met Leu Leu Gly Ser Lys Leu Arg Ala Ala Asn
        210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
        370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Phe Gly
    530                 535                 540

Arg Lys Val Ala Ser Thr Asn Ala Arg Lys Thr Thr Leu Ala Leu Glu
545                 550                 555                 560

<210> SEQ ID NO 4
<211> LENGTH: 1680
<212> TYPE: DNA
<213> ORGANISM: Artificial Sequence
<220> FEATURE:
<223> OTHER INFORMATION: Synthetic

<400> SEQUENCE: 4

| | | | | | |
|---|---|---|---|---|---|
| atgacctata | ctgttggcat | gtatcttgca | gaacgccttg | tacagatcgg | gctgaagcat | 60 |
| cacttcgccg | tggcgggcga | ctacaatctc | gttcttctgg | atcagttgct | cctcaacaag | 120 |
| gacatgaaac | agatctattg | ctgcaatgag | ttgaactgtg | gcttcagcgc | ggaaggctac | 180 |
| gcccgttcta | acggggctgc | ggcagcggtt | gtcaccttca | gcgttggcgc | catttccgcc | 240 |
| atgaacgccc | tcgcggcgc | ctatgccgaa | aacctgccgg | ttatcctgat | ttccggcgcg | 300 |
| cccaacagca | tgatcaggg | cacaggtcat | atcctgcatc | acacaatcgg | caagacggat | 360 |
| tacagctacc | agcttgaaat | ggcccgtcag | gtcacctgtg | ccgccgaaag | cattaccgac | 420 |
| gctcactccg | ccccggccaa | gattgaccac | gtcattcgca | cggcgctgcg | cgagcgtaag | 480 |
| ccggcctatc | tggacatcgc | gtgcaacatt | gcctccgagc | cctgcgtgcg | gcctggccct | 540 |
| gtcagcagcc | tgctgtccga | gcctgaaatc | gaccacacga | gcctgaaggc | cgcagtggac | 600 |
| gccacggttg | ccttgctgga | aaaatcggcc | agccccgtca | tgctgctggg | cagcaagctg | 660 |
| cgggccgcca | acgcactggc | cgcaaccgaa | acgctggcag | acaagctgca | atgcgcggtg | 720 |
| accatcatgg | cggccgcgaa | aggcttttc | cccgaagacc | acgcgggttt | ccgcggcctg | 780 |
| tactggggcg | aagtctcgaa | ccccggcgtg | caggaactgg | tggagacctc | cgacgcactg | 840 |
| ctgtgcatcg | ccccgtatt | caacgactat | tcaacagtcg | gctggtcggc | atggcccaag | 900 |
| ggccccaatg | tgattctggc | tgagcccgac | cgcgtaacgg | tcgatggccg | cgcctatgac | 960 |
| ggctttaccc | tgcgcgcctt | cctgcaggct | ctggcggaaa | aagcccccgc | gcgcccggcc | 1020 |
| tccgcacaga | aaagcagcgt | cccgacgtgc | tcgctcaccg | cgacatccga | tgaagccggt | 1080 |
| ctgacgaatg | acgaaatcgt | ccgtcatatc | aacgccctgc | tgacatcaaa | cacgacgctg | 1140 |
| gtggcagaaa | ccggcgattc | atggttcaat | gccatgcgca | tgaccctgcc | gcgcggtgcg | 1200 |
| cgcgtggaac | tggaaatgca | gtggggccat | atcggctggt | ccgtgccctc | cgccttcggc | 1260 |
| aatgccatgg | gctcgcagga | ccgccagcat | gtggtgatgg | taggcgatgg | ctccttccag | 1320 |
| cttaccgcgc | aggaagtggc | tcagatggtg | cgctacgaac | tgcccgtcat | tatctttctg | 1380 |
| atcaacaacc | gtggctatgt | cattggcatc | gccattcatg | acggcccgta | caactatatc | 1440 |
| aagaactggg | attacgccgg | cctgatggaa | gtcttcaacg | ccggagaagg | ccatggactt | 1500 |
| ggcctgaaag | ccaccacccc | gaaggaactg | acagaagcca | tcgccagggc | aaaagccaat | 1560 |
| acccgcggcc | cgacgctgat | cgaatgccag | atcgaccgca | cggactgcac | ggatatgctg | 1620 |
| gttcaatttg | gccgcaaggt | tgcctcaacc | aacgcgcgca | agaccactct | ggccctcgag | 1680 |

<210> SEQ ID NO 5
<211> LENGTH: 560
<212> TYPE: PRT
<213> ORGANISM: Artificial Sequence
<220> FEATURE:
<223> OTHER INFORMATION: Synthetic

<400> SEQUENCE: 5

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
                100                 105                 110

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
```

```
                    405                 410                 415
Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
    450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Pro Gly
    530                 535                 540

Arg Lys Val Ala Ser Thr Asn Ala Arg Lys Thr Thr Leu Ala Leu Glu
545                 550                 555                 560
```

<210> SEQ ID NO 6
<211> LENGTH: 1680
<212> TYPE: DNA
<213> ORGANISM: Artificial Sequence
<220> FEATURE:
<223> OTHER INFORMATION: Synthetic

<400> SEQUENCE: 6

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca gcgttggcgc catttccgcc     240
atgaacgccc tcggcggcgc ctatgccgaa aacctgccgg ttatcctgat ttccggcgcg     300
cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaaatcggcc agccccgtca tgctgctggg cagcaagctg     660
cgggccgcca cgcactggc cgcaaccgaa acgctggcag acaagctgca atgcgcggtg     720
accatcatgg cggccgcgaa aggctttttc cccgaagacc acgcgggttt ccgcggcctg     780
tactggggcg aagtctcgaa ccccggcgtg caggaactgg tggagacctc cgacgcactg     840
ctgtgcatcg cccccgtatt caacgactat tcaacagtcg gctggtcggc atggcccaag     900
ggccccaatg tgattctggc tgagcccgac cgcgtaacgg tcgatggccg cgcctatgac     960
ggctttaccc tgcgcgcctt cctgcaggct ctggcgaaaa agcccccgc gcgcccggcc    1020 tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc gcgcggtgcg    1200
```

```
cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaacccg ccgcaaggt tgcctcaacc aacgcgcgca agaccactct ggccctcgag    1680
```

<210> SEQ ID NO 7
<211> LENGTH: 560
<212> TYPE: PRT
<213> ORGANISM: Artificial Sequence
<220> FEATURE:
<223> OTHER INFORMATION: Synthetic

<400> SEQUENCE: 7

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285
```

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ile Gly
    530                 535                 540

Arg Lys Val Ala Ser Thr Asn Ala Arg Lys Thr Thr Leu Ala Leu Glu
545                 550                 555                 560

<210> SEQ ID NO 8
<211> LENGTH: 1680
<212> TYPE: DNA
<213> ORGANISM: Artificial Sequence
<220> FEATURE:
<223> OTHER INFORMATION: Synthetic

<400> SEQUENCE: 8
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca gcgttggcgc catttccgcc     240
atgaacgccc tcggcggcgc ctatgccgaa aacctgccgg ttatcctgat ttccggcgcg     300
cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540

```
gtcagcagcc tgctgtccga gcctgaaatc gaccacacga gcctgaaggc cgcagtggac       600
gccacggttg ccttgctgga aaaatcggcc agccccgtca tgctgctggg cagcaagctg       660
cgggccgcca acgcactggc cgcaaccgaa acgctggcag acaagctgca atgcgcggtg       720
accatcatgg cggccgcgaa aggctttttc cccgaagacc acgcgggttt ccgcggcctg       780
tactggggcg aagtctcgaa ccccggcgtg caggaactgg tggagacctc cgacgcactg       840
ctgtgcatcg ccccgtatt caacgactat tcaacagtcg gctggtcggc atggcccaag       900
ggccccaatg tgattctggc tgagcccgac cgcgtaacgg tcgatggccg cgcctatgac       960
ggctttaccc tgcgcgcctt cctgcaggct ctggcggaaa agcccccgc cgcgcccggcc      1020 tccgcacaga aaagcagcgt cccgacgtgc tcgctcaccg cgacatccga tgaagccggt      1080
ctgacgaatg acgaaatcgt ccgtcatatc aacgccctgc tgacatcaaa cacgacgctg      1140
gtggcagaaa ccggcgattc atggttcaat gccatgcgca tgaccctgcc gcgcggtgcg      1200
cgcgtggaac tggaaatgca gtggggccat atcggctggt ccgtgccctc cgccttcggc      1260
aatgccatgg gctcgcagga ccgccagcat gtggtgatgg taggcgatgg ctccttccag      1320
cttaccgcgc aggaagtggc tcagatggtg cgctacgaac tgcccgtcat tatctttctg      1380
atcaacaacc gtggctatgt cattggcatc gccattcatg acggcccgta caactatatc      1440
aagaactggg attacgccgg cctgatggaa gtcttcaacg ccggagaagg ccatggactt      1500
ggcctgaaag ccaccacccc gaaggaactg acagaagcca tcgccagggc aaaagccaat      1560
acccgcggcc cgacgctgat cgaatgccag atcgaccgca cggactgcac ggatatgctg      1620
gttcaaatag gccgcaaggt tgcctcaacc aacgcgcgca agaccactct ggccctcgag      1680
```

<210> SEQ ID NO 9
<211> LENGTH: 560
<212> TYPE: PRT
<213> ORGANISM: Artificial Sequence
<220> FEATURE:
<223> OTHER INFORMATION: Synthetic

<400> SEQUENCE: 9

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160
```

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Phe Leu Ile Asn Asn Arg
    450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Leu Gly
    530                 535                 540

Arg Lys Val Ala Ser Thr Asn Ala Arg Lys Thr Thr Leu Ala Leu Glu
545                 550                 555                 560

<210> SEQ ID NO 10
<211> LENGTH: 1680
<212> TYPE: DNA

<213> ORGANISM: Artificial Sequence
<220> FEATURE:
<223> OTHER INFORMATION: Synthetic

<400> SEQUENCE: 10

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca gcgttggcgc catttccgcc     240
atgaacgccc tcggcggcgc ctatgccgaa aacctgccgg ttatcctgat tccggcgcg      300
cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaatcggcc agccccgtca tgctgctggg cagcaagctg      660
cgggccgcca acgcactggc cgcaaccgaa acgctggcag acaagctgca atgcgcggtg     720
accatcatgg cggccgcgaa aggcttttc cccgaagacc acgcgggttt ccgcggcctg      780
tactggggcg aagtctcgaa ccccggcgtg caggaactgg tggagacctc cgacgcactg     840
ctgtgcatcg cccccgtatt caacgactat tcaacagtcg gctggtcggc atggcccaag     900
ggccccaatg tgattctggc tgagcccgac gcgtaacgg tcgatggccg cgcctatgac      960
ggctttaccc tgcgcgcctt cctgcaggct ctggcggaaa agcccccgc gcgcccggcc     1020
tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc gcgcggtgcg    1200
cgcgtggaac tggaaatgca gtggggccat atcggctggt ccgtgccctc gccttcggc     1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaactcg ccgcaaggt tgcctcaacc aacgcgcgca agaccactct ggccctcgag    1680
```

<210> SEQ ID NO 11
<211> LENGTH: 560
<212> TYPE: PRT
<213> ORGANISM: Artificial Sequence
<220> FEATURE:
<223> OTHER INFORMATION: Synthetic

<400> SEQUENCE: 11

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys

```
                    35                  40                  45
        Asn Glu Leu Asn Cys Gly Phe Ser Ala Glu Gly Tyr Ala Arg Ser Asn
                     50                  55                  60
        Gly Ala Ala Ala Val Val Thr Phe Ser Val Gly Ala Ile Ser Ala
         65                  70                  75                  80
        Met Asn Ala Leu Gly Ala Tyr Ala Glu Asn Leu Pro Val Ile Leu
                         85                  90                  95
        Ile Ser Gly Ala Pro Asn Ser Asn Asp Gln Gly Thr Gly His Ile Leu
                        100                 105                 110
        His His Thr Ile Gly Lys Thr Asp Tyr Ser Tyr Gln Leu Glu Met Ala
                        115                 120                 125
        Arg Gln Val Thr Cys Ala Ala Glu Ser Ile Thr Asp Ala His Ser Ala
                        130                 135                 140
        Pro Ala Lys Ile Asp His Val Ile Arg Thr Ala Leu Arg Glu Arg Lys
        145                 150                 155                 160
        Pro Ala Tyr Leu Asp Ile Ala Cys Asn Ile Ala Ser Glu Pro Cys Val
                        165                 170                 175
        Arg Pro Gly Pro Val Ser Ser Leu Leu Ser Glu Pro Glu Ile Asp His
                        180                 185                 190
        Thr Ser Leu Lys Ala Ala Val Asp Ala Thr Val Ala Leu Leu Glu Lys
                        195                 200                 205
        Ser Ala Ser Pro Val Met Leu Leu Gly Ser Lys Leu Arg Ala Ala Asn
        210                 215                 220
        Ala Leu Ala Ala Thr Glu Thr Leu Ala Asp Lys Leu Gln Cys Ala Val
        225                 230                 235                 240
        Thr Ile Met Ala Ala Ala Lys Gly Phe Phe Pro Glu Asp His Ala Gly
                        245                 250                 255
        Phe Arg Gly Leu Tyr Trp Gly Glu Val Ser Asn Pro Gly Val Gln Glu
                        260                 265                 270
        Leu Val Glu Thr Ser Asp Ala Leu Leu Cys Ile Ala Pro Val Phe Asn
                        275                 280                 285
        Asp Tyr Ser Thr Val Gly Trp Ser Ala Trp Pro Lys Gly Pro Asn Val
                        290                 295                 300
        Ile Leu Ala Glu Pro Asp Arg Val Thr Val Asp Gly Arg Ala Tyr Asp
        305                 310                 315                 320
        Gly Phe Thr Leu Arg Ala Phe Leu Gln Ala Leu Ala Glu Lys Ala Pro
                        325                 330                 335
        Ala Arg Pro Ala Ser Ala Gln Lys Ser Ser Val Pro Thr Cys Ser Leu
                        340                 345                 350
        Thr Ala Thr Ser Asp Glu Ala Gly Leu Thr Asn Asp Glu Ile Val Arg
                        355                 360                 365
        His Ile Asn Ala Leu Leu Thr Ser Asn Thr Thr Leu Val Ala Glu Thr
                        370                 375                 380
        Gly Asp Ser Trp Phe Asn Ala Met Arg Met Thr Leu Pro Arg Gly Ala
        385                 390                 395                 400
        Arg Val Glu Leu Glu Met Gln Trp Gly His Ile Gly Trp Ser Val Pro
                        405                 410                 415
        Ser Ala Phe Gly Asn Ala Met Gly Ser Gln Asp Arg Gln His Val Val
                        420                 425                 430
        Met Val Gly Asp Gly Ser Phe Gln Leu Thr Ala Gln Glu Val Ala Gln
                        435                 440                 445
        Met Val Arg Tyr Glu Leu Pro Val Ile Ile Phe Leu Ile Asn Asn Arg
                        450                 455                 460
```

```
Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Met Gly
530                 535                 540

Arg Lys Val Ala Ser Thr Asn Ala Arg Lys Thr Thr Leu Ala Leu Glu
545                 550                 555                 560

<210> SEQ ID NO 12
<211> LENGTH: 1680
<212> TYPE: DNA
<213> ORGANISM: Artificial Sequence
<220> FEATURE:
<223> OTHER INFORMATION: Synthetic

<400> SEQUENCE: 12
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acgggctgc ggcagcggtt gtcaccttca gcgttggcgc catttccgcc     240
atgaacgccc tcggcggcgc ctatgccgaa aacctgccgg ttatcctgat ttccggcgcg     300
cccaacagca tgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaaatcggcc agccccgtca tgctgctggg cagcaagctg     660
cgggccgcca acgcactggc cgcaaccgaa acgctggcag acaagctgca atgcgcggtg     720
accatcatgg cggccgcgaa aggcttttc cccgaagacc acgcgggttt ccgcggcctg     780
tactggggcg aagtctcgaa ccccggcgtg caggaactgg tggagacctc gacgcactg     840 ctgtgcatcg cccccgtatt caacgactat tcaacagtcg gctggtcggc atggcccaag     900
ggccccaatg tgattctggc tgagcccgac gcgtaacgg tcgatggccg cgctatgac      960 ggctttaccc tgcgcgcctt cctgcaggct ctggcggaaa agccccgc gcgcccggcc    1020 tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc gcgcggtgcg    1200
cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatggaa gtcttcaacg ccggagaagg ccatggactt    1500
```

-continued

```
ggcctgaaag ccaccacccc gaaggaactg acagaagcca tcgccagggc aaaagccaat   1560
acccgcggcc cgacgctgat cgaatgccag atcgaccgca cggactgcac ggatatgctg   1620
gttcaaatgg gccgcaaggt tgcctcaacc aacgcgcgca agaccactct ggccctcgag   1680
```

<210> SEQ ID NO 13
<211> LENGTH: 560
<212> TYPE: PRT
<213> ORGANISM: Artificial Sequence
<220> FEATURE:
<223> OTHER INFORMATION: Synthetic

<400> SEQUENCE: 13

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335
```

```
Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Val Gly
    530                 535                 540

Arg Lys Val Ala Ser Thr Asn Ala Arg Lys Thr Thr Leu Ala Leu Glu
545                 550                 555                 560

<210> SEQ ID NO 14
<211> LENGTH: 1680
<212> TYPE: DNA
<213> ORGANISM: Artificial Sequence
<220> FEATURE:
<223> OTHER INFORMATION: Synthetic

<400> SEQUENCE: 14
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta cggggctgc ggcagcggtt gtcaccttca gcgttggcgc catttccgcc      240
atgaacgccc tcggcggcgc ctatgccgaa aacctgccgg ttatcctgat tccggcgcg      300 cccaacagca tgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gctgaaggc cgcagtggac     600 gccacggttg ccttgctgga aaaatcggcc agcccgtca tgctgctggg cagcaagctg     660
cgggccgcca acgcactggc cgcaaccgaa acgctggcag acaagctgca atgcgcggtg     720
accatcatgg cggccgcgaa aggcttttc cccgaagacc acgcgggttt ccgcggcctg      780
tactggggcg aagtctcgaa ccccggcgtg caggaactgg tggagacctc cgacgcactg     840
```

```
ctgtgcatcg cccccgtatt caacgactat tcaacagtcg gctggtcggc atggcccaag    900
ggccccaatg tgattctggc tgagcccgac cgcgtaacgg tcgatggccg cgcctatgac    960
ggctttaccc tgcgcgcctt cctgcaggct ctggcggaaa agccccccgc gcgcccggcc   1020
tccgcacaga aaagcagcgt cccgacgtgc tcgctcaccg cgacatccga tgaagccggt   1080
ctgacgaatg acgaaatcgt ccgtcatatc aacgccctgc tgacatcaaa cacgacgctg   1140
gtggcagaaa ccggcgattc atggttcaat gccatgcgca tgaccctgcc gcgcggtgcg   1200
cgcgtggaac tggaaatgca gtggggccat atcggctggt ccgtgccctc cgccttcggc   1260
aatgccatgg gctcgcagga ccgccagcat gtggtgatgg taggcgatgg ctccttccag   1320
cttaccgcgc aggaagtggc tcagatggtg cgctacgaac tgcccgtcat tatctttctg   1380
atcaacaacc gtggctatgt cattggcatc gccattcatg acggcccgta caactatatc   1440
aagaactggg attacgccgg cctgatggaa gtcttcaacg ccggagaagg ccatggactt   1500
ggcctgaaag ccaccacccc gaaggaactg acagaagcca tcgccagggc aaaagccaat   1560
acccgcggcc cgacgctgat cgaatgccag atcgaccgca cggactgcac ggatatgctg   1620
gttcaagtcg ccgcaaggt tgcctcaacc aacgcgcgca agaccactct ggccctcgag   1680
```

<210> SEQ ID NO 15
<211> LENGTH: 560
<212> TYPE: PRT
<213> ORGANISM: Artificial Sequence
<220> FEATURE:
<223> OTHER INFORMATION: Synthetic

<400> SEQUENCE: 15

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
```

```
            210                 215                 220
Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
                275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
                355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
                515                 520                 525

Cys Gln Ile Asp Arg Thr Asp Cys Thr Asp Met Leu Val Gln Ala Gly
            530                 535                 540

Arg Lys Val Ala Ser Thr Asn Ala Arg Lys Thr Thr Leu Ala Leu Glu
545                 550                 555                 560

<210> SEQ ID NO 16
<211> LENGTH: 1680
<212> TYPE: DNA
<213> ORGANISM: Artificial Sequence
<220> FEATURE:
<223> OTHER INFORMATION: Synthetic

<400> SEQUENCE: 16
atgacctata ctgttggcat gtatcttgca gaacgccttg tacagatcgg gctgaagcat      60
cacttcgccg tggcgggcga ctacaatctc gttcttctgg atcagttgct cctcaacaag     120
```

-continued

```
gacatgaaac agatctattg ctgcaatgag ttgaactgtg gcttcagcgc ggaaggctac    180
gcccgttcta acggggctgc ggcagcggtt gtcaccttca gcgttggcgc catttccgcc    240

atgaacgccc tcggcggcgc ctatgccgaa aacctgccgg ttatcctgat ttccggcgcg    300
cccaacagca atgatcaggg cacaggtcat atcctgcatc acacaatcgg caagacggat    360
tacagctacc agcttgaaat ggcccgtcag gtcacctgtg ccgccgaaag cattaccgac    420
gctcactccg ccccggccaa gattgaccac gtcattcgca cggcgctgcg cgagcgtaag    480
ccggcctatc tggacatcgc gtgcaacatt gcctccgagc cctgcgtgcg gcctggccct    540
gtcagcagcc tgctgtccga gcctgaaatc gaccacacga gcctgaaggc cgcagtggac    600
gccacggttg ccttgctgga aaaatcggcc agccccgtca tgctgctggg cagcaagctg    660
cgggccgcca acgcactggc cgcaaccgaa acgctggcag acaagctgca atgcgcggtg    720
accatcatgg cggccgcgaa aggctttttc cccgaagacc acgcgggttt ccgcggcctg    780
tactggggcg aagtctcgaa ccccggcgtg caggaactgg tggagacctc cgacgcactg    840
ctgtgcatcg cccccgtatt caacgactat tcaacagtcg gctggtcggc atggcccaag    900
ggccccaatg tgattctggc tgagcccgac cgcgtaacgg tcgatggccg cgcctatgac    960
ggctttaccc tgcgcgcctt cctgcaggct ctggcggaaa aagcccccgc gcgcccggcc   1020
tccgcacaga aaagcagcgt cccgacgtgc tcgctcaccg cgacatccga tgaagccggt   1080
ctgacgaatg acgaaatcgt ccgtcatatc aacgccctgc tgacatcaaa cacgacgctg   1140
gtggcagaaa ccggcgattc atggttcaat gccatgcgca tgaccctgcc gcgcggtgcg   1200
cgcgtggaac tggaaatgca gtggggccat atcggctggt ccgtgccctc cgccttcggc   1260
aatgccatgg gctcgcagga ccgccagcat gtggtgatgg taggcgatgg ctccttccag   1320
cttaccgcgc aggaagtggc tcagatggtg cgctacgaac tgcccgtcat tatctttctg   1380
atcaacaacc gtggctatgt cattggcatc gccattcatg acggcccgta caactatatc   1440
aagaactggg attacgccgg cctgatggaa gtcttcaacg ccggagaagg ccatggactt   1500
ggcctgaaag ccaccacccc gaaggaactg acagaagcca tcgccagggc aaaagccaat   1560
acccgcggcc cgacgctgat cgaatgccag atcgaccgca cggactgcac ggatatgctg   1620
gttcaagccg gccgcaaggt tgcctcaacc aacgcgcgca agaccactct ggccctcgag   1680
```

```

<210> SEQ ID NO 17
<211> LENGTH: 560
<212> TYPE: PRT
<213> ORGANISM: Artificial Sequence
<220> FEATURE:
<223> OTHER INFORMATION: Synthetic

<400> SEQUENCE: 17

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95
```

```
Ile Ser Gly Ala Pro Asn Ser Asn Asp Gln Gly Thr Gly His Ile Leu
            100                 105                 110
His His Thr Ile Gly Lys Thr Asp Tyr Ser Tyr Gln Leu Glu Met Ala
        115                 120                 125
Arg Gln Val Thr Cys Ala Ala Glu Ser Ile Thr Asp Ala His Ser Ala
130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
            180                 185                 190
Thr Ser Leu Lys Ala Ala Val Asp Ala Thr Val Ala Leu Leu Glu Lys
        195                 200                 205
Ser Ala Ser Pro Val Met Leu Leu Gly Ser Lys Leu Arg Ala Ala Asn
    210                 215                 220
Ala Leu Ala Ala Thr Glu Thr Leu Ala Asp Lys Leu Gln Cys Ala Val
225                 230                 235                 240
Thr Ile Met Ala Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
        275                 280                 285
Asp Tyr Ser Thr Val Gly Trp Ser Ala Trp Pro Lys Gly Pro Asn Val
    290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
        355                 360                 365
His Ile Asn Ala Leu Leu Thr Ser Asn Thr Thr Leu Val Ala Glu Thr
    370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
        435                 440                 445
Met Val Arg Tyr Glu Leu Pro Val Ile Ile Phe Leu Ile Asn Asn Arg
    450                 455                 460
Gly Tyr Val Ile Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
            500                 505                 510
```

| | | | | | | | | | | | | |
|---|---|---|---|---|---|---|---|---|---|---|---|---|
|Ala|Ile|Ala|Arg|Ala|Lys|Ala|Asn|Thr|Arg|Gly|Pro|Thr|Leu|Ile|Glu|
| | | |515| | | |520| | | |525| |

Cys Gln Ile Asp Arg Thr Asp Cys Thr Asp Met Leu Val Gln Tyr Gly
              530                 535                 540

Arg Lys Val Ala Ser Thr Asn Ala Arg Lys Thr Thr Leu Ala Leu Glu
545                 550                 555                 560

<210> SEQ ID NO 18
<211> LENGTH: 1680
<212> TYPE: DNA
<213> ORGANISM: Artificial Sequence
<220> FEATURE:
<223> OTHER INFORMATION: Synthetic

<400> SEQUENCE: 18

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca gcgttggcgc catttccgcc     240
atgaacgccc tcggcggcgc ctatgccgaa aacctgccgg ttatcctgat tccggcgcg     300
cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gctgaaggc cgcagtggac     600
gccacggttg ccttgctgga aaaatcggcc agccccgtca tgctgctggg cagcaagctg     660
cgggccgcca acgcactggc cgcaaccgaa acgctggcag acaagctgca atgcgcggtg     720
accatcatgg cggccgcgaa aggcttttc cccgaagacc acgcgggttt ccgcggcctg     780
tactggggcg aagtctcgaa ccccggcgtg caggaactgg tggagacctc cgacgcactg     840
ctgtgcatcg cccccgtatt caacgactat tcaacagtcg gctggtcggc atggcccaag     900
ggcccccaatg tgattctggc tgagcccgac gcgtaacgg tcgatggccg cgcctatgac     960
ggctttaccc tgcgcgcctt cctgcaggct ctggcggaaa agcccccgc gcgcccggcc    1020
tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc gcgcggtgcg    1200
cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaatacg gccgcaaggt tgcctcaacc aacgcgcgca agaccactct ggccctcgag    1680
```

<210> SEQ ID NO 19
<211> LENGTH: 560
<212> TYPE: PRT

<213> ORGANISM: Artificial Sequence
<220> FEATURE:
<223> OTHER INFORMATION: Synthetic

<400> SEQUENCE: 19

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
```

```
                385                 390                 395                 400
Arg Val Glu Leu Glu Met Gln Trp Gly His Ile Gly Trp Ser Val Pro
                    405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Phe Leu Ile Asn Asn Arg
        450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Thr Gly
    530                 535                 540

Arg Lys Val Ala Ser Thr Asn Ala Arg Lys Thr Thr Leu Ala Leu Glu
545                 550                 555                 560

<210> SEQ ID NO 20
<211> LENGTH: 1680
<212> TYPE: DNA
<213> ORGANISM: Artificial Sequence
<220> FEATURE:
<223> OTHER INFORMATION: Synthetic

<400> SEQUENCE: 20
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca cgttggcgc catttccgcc      240 atgaacgccc tcggcggcgc ctatgccgaa aacctgccgg ttatcctgat tccggcgcg     300 cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaaatcggcc agccccgtca tgctgctggg cagcaagctg     660
cgggccgcca acgcactggc cgcaaccgaa acgctggcag acaagctgca atgcgcggtg     720
accatcatgg cggccgcgaa aggcttttc cccgaagacc acgcgggttt ccgcggcctg     780
tactggggcg aagtctcgaa ccccggcgtg caggaactgg tggagacctc cgacgcactg     840
ctgtgcatcg ccccgtatt caacgactat caacagtcg gctggtcggc atggcccaag     900
ggccccaatg tgattctggc tgagcccgac cgcgtaacgg tcgatggccg cgcctatgac     960
ggctttaccc tgcgcgcctt cctgcaggct ctggcggaaa agccccgc gcgcccggcc     1020 tccgcacaga aaagcagcgt cccgacgtgc tcgctcaccg cgacatccga tgaagccggt     1080
ctgacgaatg acgaaatcgt ccgtcatatc aacgccctgc tgacatcaaa cacgacgctg     1140
```

```
gtggcagaaa ccggcgattc atggttcaat gccatgcgca tgaccctgcc gcgcggtgcg    1200
cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatgaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaaacag gccgcaaggt tgcctcaacc aacgcgcgca agaccactct ggccctcgag    1680
```

<210> SEQ ID NO 21
<211> LENGTH: 560
<212> TYPE: PRT
<213> ORGANISM: Artificial Sequence
<220> FEATURE:
<223> OTHER INFORMATION: Synthetic

<400> SEQUENCE: 21

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270
```

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Gly Gly
    530                 535                 540

Arg Lys Val Ala Ser Thr Asn Ala Arg Lys Thr Thr Leu Ala Leu Glu
545                 550                 555                 560

<210> SEQ ID NO 22
<211> LENGTH: 1680
<212> TYPE: DNA
<213> ORGANISM: Artificial Sequence
<220> FEATURE:
<223> OTHER INFORMATION: Synthetic

<400> SEQUENCE: 22
atgacctata ctgttggcat gtatcttgca gaacgccttg tacagatcgg gctgaagcat        60
cacttcgccg tggcgggcga ctacaatctc gttcttctgg atcagttgct cctcaacaag       120
gacatgaaac agatctattg ctgcaatgag ttgaactgtg gcttcagcgc ggaaggctac       180
gcccgttcta acgggctgc ggcagcggtt gtcaccttca gcgttggcgc catttccgcc        240
atgaacgccc tcggcggcgc ctatgccgaa aacctgccgg ttatcctgat tccggcgcg        300 cccaacagca tgatcaggg cacaggtcat atcctgcatc acacaatcgg caagacggat        360
tacagctacc agcttgaaat ggcccgtcag gtcacctgtg ccgccgaaag cattaccgac       420

-continued

```
gctcactccg ccccggccaa gattgaccac gtcattcgca cggcgctgcg cgagcgtaag    480
ccggcctatc tggacatcgc gtgcaacatt gcctccgagc cctgcgtgcg gcctggccct    540
gtcagcagcc tgctgtccga gcctgaaatc gaccacacga gcctgaaggc cgcagtggac    600
gccacggttg ccttgctgga aaaatcggcc agccccgtca tgctgctggg cagcaagctg    660
cgggccgcca acgcactggc cgcaaccgaa acgctggcag acaagctgca atgcgcggtg    720
accatcatgg cggccgcgaa aggcttttc cccgaagacc acgcgggttt ccgcggcctg    780
tactggggcg aagtctcgaa ccccggcgtg caggaactgg tggagacctc cgacgcactg    840
ctgtgcatcg cccccgtatt caacgactat tcaacagtcg gctggtcggc atggcccaag    900
ggccccaatg tgattctggc tgagcccgac cgcgtaacgg tcgatggccg cgcctatgac    960
ggctttaccc tgcgcgcctt cctgcaggct ctggcggaaa agccccgc gcgcccggcc    1020 tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc cgcgcggtgcg    1200 cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaaggag gccgcaaggt tgcctcaacc aacgcgcgca agaccactct ggccctcgag    1680
```

<210> SEQ ID NO 23
<211> LENGTH: 560
<212> TYPE: PRT
<213> ORGANISM: Artificial Sequence
<220> FEATURE:
<223> OTHER INFORMATION: Synthetic

<400> SEQUENCE: 23

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140
```

```
Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ser Gly
530                 535                 540

Arg Lys Val Ala Ser Thr Asn Ala Arg Lys Thr Thr Leu Ala Leu Glu
545                 550                 555                 560
```

<210> SEQ ID NO 24
<211> LENGTH: 1680
<212> TYPE: DNA
<213> ORGANISM: Artificial Sequence
<220> FEATURE:
<223> OTHER INFORMATION: Synthetic

<400> SEQUENCE: 24

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acgggctgc ggcagcggtt gtcaccttca gcgttggcgc catttccgcc     240
atgaacgccc tcggcggcgc ctatgccgaa aacctgccgg ttatcctgat tccggcgcg     300
cccaacagca tgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaaatcggcc agcccgtca tgctgctggg cagcaagctg     660
cgggccgcca cgcactggc cgcaaccgaa acgctggcag acaagctgca atgcgcggtg     720
accatcatgg cggccgcgaa aggcttttc cccgaagacc acgcgggttt ccgcggcctg     780
tactggggcg aagtctcgaa ccccggcgtg caggaactgg tggagacctc cgacgcactg     840
ctgtgcatcg ccccgtatt caacgactat tcaacagtcg gctggtcggc atggcccaag     900
ggccccaatg tgattctggc tgagcccgac gcgtaacgg tcgatggccg cgcctatgac     960
ggctttaccc tgcgcgcctt cctgcaggct ctggcggaaa agcccccgc gcgcccggcc    1020
tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc cgcgcggtgcg    1200
cgcgtggaac tggaaatgca gtgggcccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cattggcatc gccattcatg acggcccgta caactatatc    1440
aagaactggg attaccgcgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaaagtg gccgcaaggt tgcctcaacc aacgcgcgca agaccactct ggccctcgag    1680
```

<210> SEQ ID NO 25
<211> LENGTH: 560
<212> TYPE: PRT
<213> ORGANISM: Artificial Sequence
<220> FEATURE:
<223> OTHER INFORMATION: Synthetic

<400> SEQUENCE: 25

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
```

```
                 20                  25                  30
Leu Asp Gln Leu Leu Asn Lys Asp Met Lys Gln Ile Tyr Cys Cys
             35                  40                  45
Asn Glu Leu Asn Cys Gly Phe Ser Ala Glu Gly Tyr Ala Arg Ser Asn
         50                  55                  60
Gly Ala Ala Ala Ala Val Val Thr Phe Ser Val Gly Ala Ile Ser Ala
 65                  70                  75                  80
Met Asn Ala Leu Gly Gly Ala Tyr Ala Glu Asn Leu Pro Val Ile Leu
                 85                  90                  95
Ile Ser Gly Ala Pro Asn Ser Asn Asp Gln Gly Thr Gly His Ile Leu
             100                 105                 110
His His Thr Ile Gly Lys Thr Asp Tyr Ser Tyr Gln Leu Glu Met Ala
         115                 120                 125
Arg Gln Val Thr Cys Ala Ala Glu Ser Ile Thr Asp Ala His Ser Ala
         130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
             165                 170                 175
Arg Pro Gly Pro Val Ser Ser Leu Leu Ser Glu Pro Glu Ile Asp His
         180                 185                 190
Thr Ser Leu Lys Ala Ala Val Asp Ala Thr Val Ala Leu Leu Glu Lys
         195                 200                 205
Ser Ala Ser Pro Val Met Leu Leu Gly Ser Lys Leu Arg Ala Ala Asn
     210                 215                 220
Ala Leu Ala Ala Thr Glu Thr Leu Ala Asp Lys Leu Gln Cys Ala Val
225                 230                 235                 240
Thr Ile Met Ala Ala Ala Lys Gly Phe Phe Pro Glu Asp His Ala Gly
                 245                 250                 255
Phe Arg Gly Leu Tyr Trp Gly Glu Val Ser Asn Pro Gly Val Gln Glu
             260                 265                 270
Leu Val Glu Thr Ser Asp Ala Leu Leu Cys Ile Ala Pro Val Phe Asn
         275                 280                 285
Asp Tyr Ser Thr Val Gly Trp Ser Ala Trp Pro Lys Gly Pro Asn Val
     290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
             325                 330                 335
Ala Arg Pro Ala Ser Ala Gln Lys Ser Ser Val Pro Thr Cys Ser Leu
         340                 345                 350
Thr Ala Thr Ser Asp Glu Ala Gly Leu Thr Asn Asp Glu Ile Val Arg
     355                 360                 365
His Ile Asn Ala Leu Leu Thr Ser Asn Thr Thr Leu Val Ala Glu Thr
     370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                 405                 410                 415
Ser Ala Phe Gly Asn Ala Met Gly Ser Gln Asp Arg Gln His Val Val
             420                 425                 430
Met Val Gly Asp Gly Ser Phe Gln Leu Thr Ala Gln Glu Val Ala Gln
         435                 440                 445
```

```
Met Val Arg Tyr Glu Leu Pro Val Ile Ile Phe Leu Ile Asn Asn Arg
    450                 455                 460
Gly Tyr Val Ile Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
                500                 505                 510
Ala Ile Ala Arg Ala Lys Ala Asn Thr Arg Gly Pro Thr Leu Ile Glu
            515                 520                 525
Cys Gln Ile Asp Arg Thr Asp Cys Thr Asp Met Leu Val Gln Cys Gly
            530                 535                 540
Arg Lys Val Ala Ser Thr Asn Ala Arg Lys Thr Thr Leu Ala Leu Glu
545                 550                 555                 560

<210> SEQ ID NO 26
<211> LENGTH: 1680
<212> TYPE: DNA
<213> ORGANISM: Artificial Sequence
<220> FEATURE:
<223> OTHER INFORMATION: Synthetic

<400> SEQUENCE: 26
```

| | | | |
|---|---|---|---|
| atgacctata ctgttggcat gtatcttgca gaacgccttg tacagatcgg gctgaagcat | | | 60 |
| cacttcgccg tggcgggcga ctacaatctc gttcttctgg atcagttgct cctcaacaag | | | 120 |
| gacatgaaac agatctattg ctgcaatgag ttgaactgtg gcttcagcgc ggaaggctac | | | 180 |
| gcccgttcta acggggctgc ggcagcggtt gtcaccttca gcgttggcgc catttccgcc | | | 240 |
| atgaacgccc tcgcggcgc ctatgccgaa aacctgccgg ttatcctgat ttccggcgcg | | | 300 |
| cccaacagca atgatcaggg cacaggtcat atcctgcatc acacaatcgg caagacggat | | | 360 |
| tacagctacc agcttgaaat ggcccgtcag gtcacctgtg ccgccgaaag cattaccgac | | | 420 |
| gctcactccg ccccggccaa gattgaccac gtcattcgca cggcgctgcg cgagcgtaag | | | 480 |
| ccggcctatc tggacatcgc gtgcaacatt gcctccgagc cctgcgtgcg gcctggccct | | | 540 |
| gtcagcagcc tgctgtccga gcctgaaatc gaccacacga gcctgaaggc cgcagtggac | | | 600 |
| gccacggttg ccttgctgga aaaatcggcc agccccgtca tgctgctggg cagcaagctg | | | 660 |
| cgggccgcca acgcactggc cgcaaccgaa acgctggcag acaagctgca atgcgcggtg | | | 720 |
| accatcatgg cggccgcgaa aggctttttc cccgaagacc acgcgggttt ccgcggcctg | | | 780 |
| tactggggcg aagtctcgaa ccccggcgtg caggaactgg tggagacctc cgacgcactg | | | 840 |
| ctgtgcatcg ccccgtatt caacgactat tcaacagtcg gctggtcggc atggcccaag | | | 900 |
| ggccccaatg tgattctggc tgagcccgac gcgtaacgg tcgatggccg cgcctatgac | | | 960 |
| ggctttaccc tgcgcgcctt cctgcaggct ctggcggaaa aagcccccgc gcgcccggcc | | | 1020 |
| tccgcacaga aaagcagcgt cccgacgtgc tcgctcaccg cgacatccga tgaagccggt | | | 1080 |
| ctgacgaatg acgaaatcgt ccgtcatatc aacgccctgc tgacatcaaa cacgacgctg | | | 1140 |
| gtggcagaaa ccggcgattc atggttcaat gccatgcgca tgaccctgcc gcgcggtgcg | | | 1200 |
| cgcgtggaac tggaaatgca gtggggccat atcggctggt ccgtgccctc cgccttcggc | | | 1260 |
| aatgccatgg gctcgcagga ccgccagcat gtggtgatgg taggcgatgg ctccttccag | | | 1320 |
| cttaccgcgc aggaagtggc tcagatggtg cgctacgaac tgcccgtcat tatctttctg | | | 1380 |
| atcaacaacc gtggctatgt cattggcatc gccattcatg acgcccgta caactatatc | | | 1440 |

```
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaatgtg gccgcaaggt tgcctcaacc aacgcgcgca agaccactct ggccctcgag    1680

<210> SEQ ID NO 27
<211> LENGTH: 7041
<212> TYPE: DNA
<213> ORGANISM: Artificial Sequence
<220> FEATURE:
<223> OTHER INFORMATION: Synthetic

<400> SEQUENCE: 27
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta aagggatttt gccgatttcg gcctattggt taaaaaatg agctgattta     420 acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc cttttttgata atctcatgac    1560 caaaatccct taacgtgagt tttcgttcca ctgagcgtca gaccccgtag aaaagatcaa    1620
aggatcttct tgagatcctt ttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
```

```
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt tggtggcgg    3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
```

```
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt taactttaag aaggagatat acatatgacc tatactgttg    5220
gcatgtatct tgcagaacgc cttgtacaga tcgggctgaa gcatcacttc gccgtggcgg    5280
gcgactacaa tctcgttctt ctggatcagt tgctcctcaa caaggacatg aaacagatct    5340
attgctgcaa tgagttgaac tgtggcttca gcgcggaagg ctacgcccgt tctaacgggg    5400
ctgcggcagc ggttgtcacc ttcagcgttg gcgccatttc cgccatgaac gccctcggcg    5460
gcgcctatgc cgaaaacctg ccggttatcc tgatttccgg cgcgcccaac agcaatgatc    5520
agggcacagg tcatatcctg catcacacaa tcggcaagac ggattacagc taccagcttg    5580
aaatggcccg tcaggtcacc tgtgccgccg aaagcattac cgacgctcac tccgccccgg    5640
ccaagattga ccacgtcatt cgcacggcgc tgcgcgagcg taagccggcc tatctggaca    5700
tcgcgtgcaa cattgcctcc gagccctgcg tgcggcctgg ccctgtcagc agcctgctgt    5760
ccgagcctga aatcgaccac acgagcctga aggccgcagt ggacgccacg gttgccttgc    5820
tggaaaaatc ggccagcccc gtcatgctgc tgggcagcaa gctgcgggcc gccaacgcac    5880
tggccgcaac cgaaacgctg gcagacaagc tgcaatgcgc ggtgaccatc atggcggccg    5940
cgaaaggctt tttccccgaa gaccacgcgg gtttccgcgg cctgtactgg ggcgaagtct    6000
cgaaccccgg cgtgcaggaa ctggtggaga cctccgacgc actgctgtgc atcgcccccg    6060
tattcaacga ctattcaaca gtcggctggt cggcatggcc caagggcccc aatgtgattc    6120
tggctgagcc cgaccgcgta acggtcgatg ccgcgccta tgacggcttt accctgcgcg    6180
ccttcctgca ggctctggcg gaaaaagccc ccgcgcgccc ggcctccgca cagaaaagca    6240
gcgtcccgac gtgctcgctc accgcgacat ccgatgaagc cggtctgacg aatgacgaaa    6300
tcgtccgtca tatcaacgcc ctgctgacat caaacacgac gctggtggca gaaaccggcg    6360
attcatggtt caatgccatg cgcatgaccc tgccgcgcgg tgcgcgcgtg gaactggaaa    6420
tgcagtgggg ccatatcggc tggtccgtgc cctccgcctt cggcaatgcc atgggctcgc    6480
aggaccgcca gcatgtggtg atggtaggcg atggctcctt ccagcttacc gcgcaggaag    6540
```

| | |
|---|---:|
| tggctcagat ggtgcgctac gaactgcccg tcattatctt tctgatcaac aaccgtggct | 6600 |
| atgtcattgg catcgccatt catgacggcc cgtacaacta tcaagaac tgggattacg | 6660 |
| ccggcctgat ggaagtcttc aacgccggag aaggccatgg acttggcctg aaagccacca | 6720 |
| cccgaagga actgacagaa gccatcgcca gggcaaaagc caatacccgc ggcccgacgc | 6780 |
| tgatcgaatg ccagatcgac cgcacggact gcacggatat gctggttcaa catggccgca | 6840 |
| aggttgcctc aaccaacgcg cgcaagacca ctctggccct cgagcaccac caccaccac | 6900 |
| actgagatcc ggctgctaac aaagcccgaa aggaagctga gttggctgct gccaccgctg | 6960 |
| agcaataact agcataaccc cttggggcct ctaaacgggt cttgagggg ttttgctga | 7020 |
| aaggaggaac tatatccgga t | 7041 |

<210> SEQ ID NO 28
<211> LENGTH: 1680
<212> TYPE: DNA
<213> ORGANISM: Artificial Sequence
<220> FEATURE:
<223> OTHER INFORMATION: Synthetic

<400> SEQUENCE: 28

| | |
|---|---:|
| atgacctata ctgttggcat gtatcttgca gaacgccttg tacagatcgg gctgaagcat | 60 |
| cacttcgccg tggcgggcga ctacaatctc gttcttctgg atcagttgct cctcaacaag | 120 |
| gacatgaaac agatctattg ctgcaatgag ttgaactgtg gcttcagcgc ggaaggctac | 180 |
| gcccgttcta acgggctgc ggcagcggtt gtcaccttca gcgttggcgc catttccgcc | 240 |
| atgaacgccc tcgcggcgc ctatgccgaa aacctgccgg ttatcctgat ttccggcgcg | 300 |
| cccaacagca atgatcaggg cacaggtcat atcctgcatc acacaatcgg caagacggat | 360 |
| tacagctacc agcttgaaat ggcccgtcag gtcacctgtg ccgccgaaag cattaccgac | 420 |
| gctcactccg ccccggccaa gattgaccac gtcattcgca cggcgctgcg cgagcgtaag | 480 |
| ccggcctatc tggacatcgc gtgcaacatt gcctccgagc cctgcgtgcg gcctggccct | 540 |
| gtcagcagcc tgctgtccga gcctgaaatc gaccacacga gcctgaaggc cgcagtggac | 600 |
| gccacggttg ccttgctgga aaaatcggcc agccccgtca tgctgctggg cagcaagctg | 660 |
| cgggccgcca acgcactggc cgcaaccgaa acgctggcag acaagctgca atgcgcggtg | 720 |
| accatcatgg cggccgcgaa aggcttttc cccgaagacc acgcgggttt ccgcggcctg | 780 |
| tactggggcg aagtctcgaa ccccggcgtg caggaactgg tggagacctc cgacgcactg | 840 |
| ctgtgcatcg ccccgtatt caacgactat tcaacagtcg gctggtcggc atggcccaag | 900 |
| ggccccaatg tgattctggc tgagcccgac cgcgtaacgg tcgatggccg cgcctatgac | 960 |
| ggctttaccc tgcgcgcctt cctgcaggct ctggcggaaa aagccccgc gcgcccggcc | 1020 |
| tccgcacaga aaagcagcgt cccgacgtgc tcgctcaccg cgacatccga tgaagccggt | 1080 |
| ctgacgaatg acgaaatcgt ccgtcatatc aacgccctgc tgacatcaaa cacgacgctg | 1140 |
| gtggcagaaa ccggcgattc atggttcaat gccatgcgca tgaccctgcc gcgcggtgcg | 1200 |
| cgcgtggaac tggaaatgca gtggggccat atcggctggt ccgtgccctc gccttcggc | 1260 |
| aatgccatgg gctcgcagga ccgccagcat gtggtgatgg taggcgatgg ctccttccag | 1320 |
| cttaccgcgc aggaagtggc tcagatggtg cgctacgaac tgcccgtcat tatctttctg | 1380 |
| atcaacaacc gtggctatgt cattggcatc gccattcatg acggccgta caactatatc | 1440 |
| aagaactggg attaccccgg cctgatgaa gtcttcaacg ccgagaagg ccatggactt | 1500 |
| ggcctgaaag ccaccacccc gaaggaactg acagaagcca tcgccagggc aaaagccaat | 1560 |

```
acccgcggcc cgacgctgat cgaatgccag atcgaccgca cggactgcac ggatatgctg    1620
gttcaatggg gccgcaaggt tgcctcaacc aacgcgcgca agaccactct ggccctcgag    1680
```

<210> SEQ ID NO 29
<211> LENGTH: 560
<212> TYPE: PRT
<213> ORGANISM: Artificial Sequence
<220> FEATURE:
<223> OTHER INFORMATION: Synthetic

<400> SEQUENCE: 29

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
```

```
                    340              345              350
Thr Ala Thr Ser Asp Glu Ala Gly Leu Thr Asn Asp Glu Ile Val Arg
            355                  360                  365
His Ile Asn Ala Leu Leu Thr Ser Asn Thr Thr Leu Val Ala Glu Thr
        370                  375                  380
Gly Asp Ser Trp Phe Asn Ala Met Arg Met Thr Leu Pro Arg Gly Ala
385                  390                  395                  400
Arg Val Glu Leu Glu Met Gln Trp Gly His Ile Gly Trp Ser Val Pro
                405                  410                  415
Ser Ala Phe Gly Asn Ala Met Gly Ser Gln Asp Arg Gln His Val Val
            420                  425                  430
Met Val Gly Asp Gly Ser Phe Gln Leu Thr Ala Gln Glu Val Ala Gln
        435                  440                  445
Met Val Arg Tyr Glu Leu Pro Val Ile Ile Phe Leu Ile Asn Asn Arg
    450                  455                  460
Gly Tyr Val Ile Gly Ile Ala Ile His Asp Gly Pro Tyr Asn Tyr Ile
465                  470                  475                  480
Lys Asn Trp Asp Tyr Ala Gly Leu Met Glu Val Phe Asn Ala Gly Glu
                485                  490                  495
Gly His Gly Leu Gly Leu Lys Ala Thr Thr Pro Lys Glu Leu Thr Glu
            500                  505                  510
Ala Ile Ala Arg Ala Lys Ala Asn Thr Arg Gly Pro Thr Leu Ile Glu
        515                  520                  525
Cys Gln Ile Asp Arg Thr Asp Cys Thr Asp Met Leu Val Gln Trp Gly
    530                  535                  540
Arg Lys Val Ala Ser Thr Asn Ala Arg Lys Thr Thr Leu Ala Leu Glu
545                  550                  555                  560
```

<210> SEQ ID NO 30
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: n is a, c, g, or t

<400> SEQUENCE: 30
ggatatgctg gttcaandtg gccgcaaggt tgc          33

<210> SEQ ID NO 31
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is a, c, g, or t

<400> SEQUENCE: 31
ggcaaccttg cggccahntt gaaccagcat atc          33

LYASE AND LYASE-ENCODING DNA, VECTORS CONTAINING THE DNA, AND METHOD FOR THE ASYMMETRIC SYNTHESIS OF (S)-PHENYLACETYLCARBINOL

CROSS-REFERENCE TO PRIOR APPLICATIONS

This application is a U.S. National Phase application under 35 U.S.C. § 371 of International Application No. PCT/DE2015/000407, filed on Aug. 14, 2015, and claims benefit to German Patent Application No. DE 10 2014 013 644.2, filed on Sep. 16, 2014. The International Application was published in German on Mar. 24, 2016 as WO 2016/041533 A1 under PCT Article 21 (2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 110,279 bytes ASCII (Text) file named "815656SequenceListing_ST25," created Mar. 2, 2017.

FIELD

The invention relates to a lyase and to a DNA encoding the lyase, to vectors containing the DNA, and to a method for the asymmetric synthesis of (S)-phenylacetylcarbinol.

BACKGROUND (S)-Phenylacetylcarbinol is a valuable chiral building block in organic syntheses and can be used for synthesis of fine chemicals and pharmaceuticals. According to the prior art to date, no methods are known in which (S)-phenylacetylcarbinol (S)-PAC can be generated in optical purities of >89% ee by asymmetric synthesis from non-chiral, inexpensive compounds. However, high optical purities are of decisive importance in the production of fine chemicals or pharmaceuticals.

According to the prior art, various methods are known for producing (S)-phenylacetylcarbinol.

On the one hand chemical syntheses are known.

The methods for producing (S)-PAC based on chemical asymmetric synthesis generate an ee of 68% or 86%. The methods are described in the publications of Davis, Franklin A.; Sheppard, Aurelia C; Lal, G. Sankar Tetrahedron Letters, 1989, vol. 30, 7 p. 779-782 and Adam, Waldemar; Fell, Rainer T.; Stegmann, Veit R.; Saha-Moeller, Chantu R. Journal of the American Chemical Society, 1998, vol. 120, 4 p. 708-714. There are furthermore methods in which (S)-PAC is formed only as a by-product and (R)-PAC is present in an enantiomeric excess, such as for example in the following reactions, such as the reduction of 1-phenylpropane-1,2-dione, which is described in the publications of Toukoniitty, Esa; Maeki-Arvela, Paeivi; Kuzma, Marek; Villela, Alexandre; Kalantar Neyestanaki, Ahmad; Salmi, Tapio; Sjoeholm, Rainer; Leino, Reko; Laine, Ensio; Murzin, Dmitry Yu, Journal of Catalysis, 2001, vol. 204, 2 p. 281-291, and the synthesis starting from benzaldehyde, which is described by Fleming, Steven A.; Carroll, Sean M.; Hirschi, Jennifer; Liu, Renmao; Pace, J. Lee; Redd, J. Ty Tetrahedron Letters, 2004, vol. 45, 17 p. 3341-3343, and the reaction of 2-hydroxy-2-phenylacetonitrile of Brussee, J.; Roos, E. C; Gen, A. Van Der Tetrahedron Letters, 1988, vol. 29, 35 p. 4485-4488.

A synthesis is moreover described in which the chiral building block 1-phenylpropane-1,2-diol can be oxidized to (S)-PAC. (S)-PAC is formed with an enantiomeric excess (ee) of 91%, as described by Zi-Qiang Rong, Hui-Jie Pan, Hai-Long Yan, and Yu Zhao Organic Letters, 2014, 16 (1), pp 208-211, or 69%, as has been described by Waldemar Adam, Chantu R. Saha-Möller, and Cong-Gui Zhao Journal of Organic Chemistry, 64 (20), 7492-7497; 1999, but in addition is contaminated with a regioisomer which must be separated off in a cumbersome manner.

An enzymatic asymmetric synthesis is furthermore known, which is described in the 2013 dissertation of Álvaro Gómez Baraibar entitled "Development of a biocatalytic production process for (S)-alpha-hydroxy ketones". If this enzyme expressed according to this dissertation heterologously in *Escherichia coli* is used for the synthesis in whole cells, the optical purity of (S)-PAC is ~43% ee.

This sole enzymatic asymmetric synthesis of (S)-PAC was described in a carboligation reaction starting from benzaldehyde and acetaldehyde, or benzaldehyde and pyruvate. The reaction is catalyzed by a variant of the enzyme pyruvate decarboxylase from *Acetobacter pasteurianus*, ApPDC-E469G, in which glutamate is replaced by glycine in position 469. The highest enantiomeric excess which has been achieved with the isolated enzyme in this context is 89%, as described by Rother Nee Gocke, Doerte; Kolter, Geraldine; Gerhards, Tina; Berthold, Catrine L.; Gauchenova, Ekaterina; Knoll, Michael; Pleiss, Juergen; Mueller, Michael; Schneider, Gunter; Pohl, Martina in the publication in ChemCatChem, 2011, vol. 3, 10 p. 1587-1596.

SUMMARY

In an embodiment, the present invention provides a lyase, comprising an amino acid sequence according to SEQ ID NO: 1, 3, 9 or 21.

BRIEF DESCRIPTION OF THE DRAWINGS

FIG. 1 shows a plasmid according to an embodiment of the invention (pET-21a(+) vector map).

DETAILED DESCRIPTION

In an embodiment, the present invention provides an enzymatic method for the asymmetric synthesis of (S)-phenylacetylcarbinol which renders possible a higher enantiomeric excess of (S)-phenylacetylcarbinol. The enantiomeric excess of (S)-phenylacetylcarbinol is to be higher than 89%. In a production with whole cells, the enantiomeric excess is to be greater than 43%. Furthermore, no by-products and no regioisomers are to be formed. It is to be possible in this context to employ inexpensive educts which are not chiral. An asymmetric synthesis of (S)-phenylacetylcarbinol is to be rendered possible. Expensive separation of chiral product mixtures is to be prevented.

An enzyme with which (S)-phenylacetylcarbinol can be produced from benzaldehyde and pyruvate or acetaldehyde and a DNA encoding the enzyme and a vector containing the DNA are to be provided.

Furthermore, a method for producing the enzyme is provided.

A method for producing (S)-phenylacetylcarbinol which also renders possible high enantiomeric excesses when crude cell extracts or whole cells are employed is to be provided.

Certain embodiments of the invention provide a variant of the lyase ApPDC-E469G in which the tryptophan in position 543 is replaced by an amino acid which is sterically smaller, or fills a reduced space with respect to tryptophan, and deoxyribonucleic acids encoding this and vectors which contain these deoxyribonucleic acids. These lyases are employed according to other embodiments for reacting benzaldehyde with pyruvate or acetaldehyde to give (S)-phenylacetylcarbinol.

With these embodiments, the DNA encoding them, the vector and the method for producing (S)-phenylacetylcarbinol, it is now possible to produce (S)-phenylacetylcarbinol in an enantiomeric excess of 97% ee using the isolated enzyme, of 95% ee using whole cells and of 94% ee using a crude cell extract. No by-products, in particular no regioisomers are formed. As a result of the synthesis being carried out with non-chiral educts, it is inexpensive. Separation of enantiomers can be dispensed with. High enantiomeric excesses can also be achieved in the production of (S)-phenylacetylcarbinol with crude cell extracts or whole cells.

According to an embodiment of the invention, a lyase is provided in which the tryptophan in position 543 in the protein ApPDC-E469G, which is modified with respect to the wild type from *Acetobacter pasteurianus*, is replaced by an amino acid which is sterically smaller than tryptophan, or less space-filling than tryptophan.

This lyase has a positive influence on the increase in the stereoselectivity in the preparation of (S)-phenylacetylcarbinol.

The following lyases which meet this requirement may be mentioned as preferred:

ApPDC-E469G-W543H according to SEQ ID NO: 1 with histidine in position 543

ApPDC-E469G-W543F according to SEQ ID NO: 3 with phenylalanine in position 543

ApPDC-E469G-W543P according to SEQ ID NO: 5 with proline in position no. 543

ApPDC-E469G-W543I according to SEQ ID NO: 7 with isoleucine in position no. 543

ApPDC-E469G-W543L according to SEQ ID NO: 9 with leucine in position no. 543

ApPDC-E469G-W543M according to SEQ ID NO: 11 with methionine in position no. 543

ApPDC-E469G-W543V according to SEQ ID NO: 13 with valine in position 543

ApPDC-E469G-W543A according to SEQ ID NO: 15 with alanine in position no. 543

ApPDC-E469G-W543Y according to SEQ ID NO: 17 with tyrosine in position no. 543

ApPDC-E469G-W543T according to SEQ ID NO: 19 with threonine in position 543

ApPDC-E469G-W543G according to SEQ ID NO: 21 with glycine in position no. 543

ApPDC-E469G-W543S according to SEQ ID NO: 23 with serine in position no. 543

ApPDC-E469G-W543C according to SEQ ID NO: 25 with cysteine in position no. 543

Deoxyribonucleic acids which encode the enzymes mentioned are furthermore provided according to embodiments of the invention.

According to an embodiment of the invention, these are deoxyribonucleic acids which encode a variant of the enzyme ApPDC-E469G which in position 1627-1629 encode an amino acid which fills a reduced space with respect to tryptophan.

Preferably, the deoxyribonucleic acid encodes the proteins according to SEQ ID NOs: 1, 3, 5, 7, 9, 11, 13, 15, 17, 19, 21, 23 and 25.

The following deoxyribonucleic acids may be mentioned by way of example.

SEQ ID NO: 2 encoding ApPDC-E469G-W543H
SEQ ID NO: 4 encoding ApPDC-E469G-W543F
SEQ ID NO: 6 encoding ApPDC-E469G-W543P
SEQ ID NO: 8 encoding ApPDC-E469G-W543I
SEQ ID NO: 10 encoding ApPDC-E469G-W543L
SEQ ID NO: 12 encoding ApPDC-E469G-W543M
SEQ ID NO: 14 encoding ApPDC-E469G-W543V
SEQ ID NO: 16 encoding ApPDC-E469G-W543A
SEQ ID NO: 18 encoding ApPDC-E469G-W543Y
SEQ ID NO: 20 encoding ApPDC-E469G-W543T
SEQ ID NO: 22 encoding ApPDC-E469G-W543G
SEQ ID NO: 24 encoding ApPDC-E469G-W543S
SEQ ID NO: 26 encoding ApPDC-E469G-W543C For the example according to SEQ ID NO: 2, in which the amino acid histidine is encoded in this position, the nucleic acids TGG, for example, can be in positions 1627-1629.

In one embodiment of the invention, the deoxyribonucleic acids are ligated into a vector, preferably a plasmid.

Empty vectors which can be employed are, for example, pET-20b(+), pET-21a-d(+), pET-22b(+), pET-23a-d(+), pET-24a-d(+), pET-25b(+), pET-26b(+), pET-27b(+), pET-28a(+), pET-29a-c(+), pET-30a-c(+), pET-31b(+), pET-34b(+), pET-35b(+), pET-36b(+), pET-37b(+), pET-38b(+), into which the corresponding DNA according to the invention is ligated.

Alternatively, the deoxyribonucleic acids can also be ligated into the genome.

The ligated deoxyribonucleic acids are a DNA sequence which encodes a variant of the enzyme ApPDC-E469G and which in position 1627-1629 encode an amino acid which fills a reduced space with respect to tryptophan.

Preferably, the ligated deoxyribonucleic acid encodes the proteins according to SEQ ID NOS: 1, 3, 5, 7, 9, 11, 13, 15, 17, 19, 21, 23 and 25.

Deoxyribonucleic acids according to the SEQ ID NOS: 2, 4, 6, 8, 10, 12, 14, 16, 18, 20, 22, 24 and 26 may be mentioned by way of example.

According to certain embodiments of the invention, vectors are provided which contain a deoxyribonucleic acid which encodes a variant of the enzyme ApPDC-E469G and which in position 1627-1629 encodes an amino acid which fills a reduced space with respect to tryptophan.

Preferably, the vector contains a deoxyribonucleic acid according to one of the SEQ ID NOs: 2, 4, 6, 8, 10, 12, 14, 16, 18, 20, 22, 24 or 26.

Preferably, the vector is a plasmid.

SEQ ID NO: 27 is by way of example a DNA sequence for a plasmid according to the invention which contains a DNA according to SEQ ID NO: 2.

A DNA encoding the enzymes according to certain embodiments of the invention can be produced by directed or non-directed mutagenesis by methods known to a person skilled in the art. Directed mutagenesis is preferred in this context. These methods are known to a person skilled in the art. An example of producing an embodiment of the invention is disclosed concretely in the detailed description section. This procedure can also be employed in principle for all the other deoxyribonucleic acids and enzymes disclosed, so that all the enzymes and deoxyribonucleic acids according to certain embodiments of the invention can be produced in an analogous manner.

According to certain embodiments of the invention, benzaldehyde is reacted with pyruvate or with acetaldehyde according to formula (1) by means of a variant of the enzyme ApPDC-E469G, which has in position 543 an amino acid which fills a reduced space with respect to tryptophan, preferably an enzyme from the group according to SEQ ID NOs: 1, 3, 5, 7, 9, 11, 13, 15, 17, 19, 21, 23 or 25, to give (S)-phenylacetylcarbinol.

Formula (1)

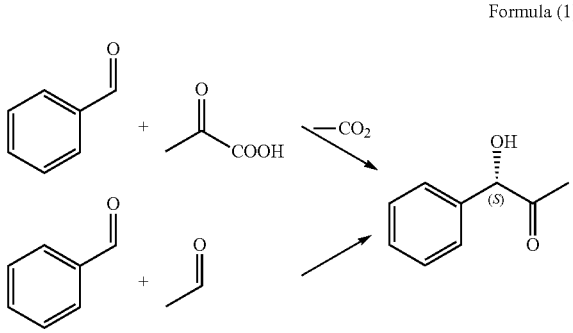

The reaction is preferably carried out in aqueous solution.

The pH is in a range of 5-9, preferably 6.5-8, particularly preferably 6.5-7.

In this reaction, potassium phosphate buffer, HEPES, MOPS, TEA or TRIS-HCl, for example, can be employed as a buffer.

Thiamine diphosphate and magnesium sulfate can furthermore be employed as cofactors.

The reaction can be carried out in vivo or in vitro.

For the in vivo production of (S)-phenylacetylcarbinol, for example, *E. coli*, a *Corynebacterium*, for example *Corynebacterium glutamicum*, or a yeast, such as *Saccharomyces cerevisiae*, can be employed as the production organism.

For this production, the production organisms are transformed with the DNA according to certain embodiments of the invention or a vector which contains the DNA.

The DNA can also be introduced into the genome in the production organism.

The genes employed according to certain embodiments of the invention are expressed heterologously in this context.

For the in vitro production either the isolated enzyme or the cell extract of the production organisms can be employed.

Typical temperatures are between 20° C. and 40° C., 20° C. to 30° C. are preferred and a temperature of from 20° C. to 25° C. is particularly preferred.

The reaction times can be 2 h-48 h, preferably 6 h-24 h, particularly preferably 12 h.

Some examples, which are not to be interpreted as limiting, are described in the following.

The reactions can be carried out in a conventional set-up in a reaction flask with stirring.

Example 1

20 mM benzaldehyde, 400 mM pyruvate, 2.5 mM magnesium sulfate, 100 μM thiamine diphosphate, 5 mg/ml of ApPDC-E469G-W543H (crude cell extract of *E. coli* cells in which ApPDC-E469G-W543H was expressed), 50 mM potassium phosphate buffer pH 6.5, 25° C., reaction time: 48 h.

Enantiomeric purity of (S)-PAC: ee 94%

Example 2

20 mM benzaldehyde, 400 mM pyruvate, 2.5 mM magnesium sulfate, 100 μM thiamine diphosphate, 20 mg/ml (moist weight) of ApPDC-E469G-W543H (whole cells of *E. coli* in which ApPDC-E469G-W543H was expressed), 50 mM potassium phosphate buffer pH 6.5, 25° C., reaction time: 48 h.

Enantiomeric purity of (S)-PAC: ee 95%
Yield: 68%

Example 3

20 mM benzaldehyde, 400 mM pyruvate, 2.5 mM magnesium sulfate, 100 μM thiamine diphosphate, 1 mg/ml of ApPDC-E469G-W543H (isolated enzyme), 50 mM potassium phosphate buffer pH 6.5, 25° C., reaction time: 48 h.

Enantiomeric purity of (S)-PAC: ee 97%
Yield: 64%

The variant ApPDC-E469G-W543H produces (S)-PAC using isolated enzymes with an ee of 97%. Using ApPDC-E469G-W543H, which was expressed heterologously in *Escherichia coli* and is employed as an inexpensive whole cell catalyst, (S)-PAC with an ee of 95% can be generated. Use as a cell extract with the ApPDC-E469G-W543H variant expressed heterologously in *E. coli* leads to an ee of 94%.

The production of the deoxyribonucleic acid which encodes the enzyme ApPDC-E469G-W543H and of the enzyme is described more precisely in the following.

The method of site saturated mutagenesis according to the variant of Reetz et al. (M. T. Reetz, D. Kahakeaw and R. Lohmer, *Chem Bio Chem*, 2008 (9) 1797-1804) was carried out starting from the gene sequence ApPDC-E469G (template DNA) in order to obtain amino acid replacements at position W543. NDT codons which encode 12 out of 20 natural amino acids are used in this method.

Polymerase Chain Reaction (PCR)

In an initial step, the template DNA is multiplied by means of the polymerase chain reaction (PCR) and at the same time mutations are introduced here by using degenerated primers and NDT codons. The primers used were obtained from "Eurofins MWG Operon" (see eurofins genomics website) and had the following sequence:

Primers for Site Saturated Mutagenesis for Producing ApPDC-E469G-W543NDT

```
                                       (SEQ ID NO: 30)
forward:    5'GGATATGCTGGTTCAANDTGGCCGCAAGGTTGC 3

(SEQ ID NO: 31)
reverse:    5'GGCAACCTTGCGGCCAHNTTGAACCAGCATATC 3'
```

A master solution was first prepared and then divided into four batches of 50 μl each. To start the reaction 1 μl of KOD Hot Start Polymerase was added.

PCR Reaction Batch:
1 portion of PCR buffer
5% (v/v) of DMSO
2 mM $MgSO_4$
0.2 mM nucleotides
0.25 pmol of forward primer 0.25 pmol of reverse primer
0.1 ng/µl of DNA template
The reaction was carried out under the following conditions:

|  | Duration (min) | Temperature (° C.) | Repetitions |
|---|---|---|---|
| Initialization | 2:00 | 95 | 20x |
| Denaturing | 2:00 | 95 |  |
| Annealing | 1:00 | 75.5° C. |  |
| Elongation | 6:00 | 70 |  |
| Termination | 10:00 | 70 |  |

To digest the template DNA, 1 µl of the enzyme Dpnl (Eppendorf) was added to the solution and the batch was incubated at 37° C. for 1 h. The entire batch was then purified with the DNA Purification Kit (list of chemicals) before the further transformation.

Transformation of E. coli BL21-DE3 and E. coli DH5α

The strains E. coli BL21-DE3 and E. coli DH5α were transformed with the DNA produced by site saturation mutagenesis. For this, 100 ng of the DNA were added to 50 µl of competent cells and the batch was incubated on ice for 30 min. A heat shock was then carried out at 42° C. for 90 sec. After 3 min on ice, 500 µl of SOC medium were added and the solution was then incubated in an Eppendorf Thermomixer at 350 rpm and 37° C. for 45 min. After the incubation had been carried out, the cell suspension was centrifuged at 13,000 rpm in an Eppendorf bench centrifuge for 30 sec and the pellet was then resuspended in 100 µl of supernatant. The cell suspension, which had been concentrated to 100 µl, was plated out on LB agar plates (with 100 µg/ml of ampicillin) and the plates were incubated upside-down at 37° C. for 16 h.

Expression of the Enzyme Variants 46 individual colonies of the transformation were picked from the plate with a toothpick and were each incubated in a well of a 48-well Nerbe plate (Nerbe Plus GmbH) with 1 ml each of LB medium at 20° C. and 850 rpm for 24 h (master plate). A further well was inoculated with E. coli BL21-DE3 cells which had been transformed analogously beforehand with the ApPDC-E469G template DNA. After the incubation had been carried out, 10 µl of the cell suspensions were added to in each case 1.5 ml of autoinduction medium in 48-well FlowerPlates® (m2p-labs, Germany). The FlowerPlate was incubated at 20° C. and 850 rpm for 48 h. 300 µl of glycerol was added to the remaining volume (990 µl) of the master plate and the mixture was stored at −80° C.

Cell Breakdown and Carboligation

The variants expressed in the FlowerPlates® (flower-like baffles in a 48-well plate) were frozen (48 h, 4° C.). After re-thawing, 500 µl portions of the cell suspensions were transferred into two wells of a 96-well plate (duplicate determination). The plate was centrifuged at 4,000 rpm for 3 min and the pellet was resuspended in 420 µl of KPi buffer with 1 mg/ml of lysozyme. The plate was incubated at 20° C. and 400 rpm for 1 h and then centrifuged again at 4,000 rpm for 10 minutes. 250 µl portions of the supernatant were each pipetted into a well of a 2 ml Nerbe plate and 250 µl of a reaction solution of 40 mM benzaldehyde, 400 mM pyruvate, 4 mM magnesium sulfate and 400 µM thiamine diphosphate were added. The plate was incubated again for 24 h and the reaction solutions were then analyzed (see HPLC analysis).

HPLC Analysis

In each case 200 µl of heptane were added to 200 µl of the carboligation reaction solutions, the mixtures were vortexed and 150 µl portions of the upper phase were then transferred into HPLC vials. The samples were analyzed with a Chiralpak IC-3 column (Chiral Technologies Inc.) using the following method.

HPLC Program

| Length | 24 min |
| Flow rate | 0.5 ml/min |
| Mobile phase | 25% isopropanol |
|  | 75% heptane |

Typical Retention Times and Wavelength Used for the Quantification

|  | Retention time (min) | Wavelength (nm |
|---|---|---|
| (R)-PAC | 12.3 | 210 |
| (S)-PAC | 12.9 | 210 |
| Benzaldehyde | 11.4 | 254 |

DNA Isolation and Identification of the Best Enzyme Variants by DNA Sequencing

The DNA of the enzyme which gave the highest ee values for (S)-PAC in the carboligation reactions was sequenced starting from the master plate for identification of the mutation. For this cells were first transferred with an inoculation loop from the master plate to which glycerol had been added into 50 ml of LB medium (+50 µg/ml of ampicillin) and the mixture was incubated at 37° C. in a 250 ml conical flask. After incubation for 12 h, 20 ml of the cell suspension were centrifuged (4,000 rpm, 5 min, 4° C.). The DNA of the cells in the pellet was isolated by the method of the QIAprep® Spin Miniprep Kit analogously to the manufacturer's instructions (Qiagen N.V.). In addition the concentration of the DNA was adjusted to 100 ng/µl and the DNA was sequenced by LGC Genomics GmbH.

LB (Lysogeny Broth) Medium

| 10 g/l | NaCl |
| 10 g/l | peptone |
| 5 g/l | yeast extract |

Alternative, Directed Method for Producing the Variant ApPDC-E469G-W543H by Means of QuikChange®

Another method for producing the enzyme variant ApPDC-E469G/W543H is, for example, the QuikChange® PCR method (U.S. Pat. Nos. 5,789,166, 5,932,419, 6,391,548). In this variant of the PCR a primer pair is used which carries the corresponding sequence modification instead of the DNA triplet code to be replaced. To produce the enzyme variant ApPDC-E469G/W543H, the gene which encodes the variant ApPDC-E469G can be used. This DNA template should be present cloned in a vector (for example pET22a). Instead of the triplet code which encodes the amino acid tryptophan in position W543, a primer which carries the histidine-encoding mutation at this position must be used (that is to say: CAC or CAT). All the further parameters of this QuikChange® PCR method and the selection of the primers required can be implemented by means of the instructions of the QuikChange® Site-Directed Mutagenesis Kit analogously to the manufacturer's information (Agilent Technologies Inc.) information.

DNA Template (ApPDC-E469G) of the QuikChange® PCR Method for Producing the Variant ApPDC-E469G-W543H

```
ATGACCTATACTGTTGGCATGTATCTTGCAGAACGCCTTGTACAGATCGG
GCTGAAGCATCACTTCGCCGTGGCGGGCGACTACAATCTCGTTCTTCTGG
ATCAGTTGCTCCTCAACAAGGACATGAAACAGATCTATTGCTGCAATGAG
TTGAACTGTGGCTTCAGCGCGGAAGGCTACGCCCGTTCTAACGGGGCTGC
GGCAGCGGTTGTCACCTTCAGCGTTGGCGCCATTTCCGCCATGAACGCCC
TCGGCGGCGCCTATGCCGAAAACCTGCCGGTTATCCTGATTTCCGGCGCG
CCCAACAGCAATGATCAGGGCACAGGTCATATCCTGCATCACACAATCGG
CAAGACGGATTACAGCTACCAGCTTGAAATGGCCCGTCAGGTCACCTGTG
CCGCCGAAAGCATTACCGACGCTCACTCCGCCCCGGCCAAGATTGACCAC
GTCATTCGCACGGCGCTGCGCGAGCGTAAGCCGGCCTATCTGGACATCGC
GTGCAACATTGCCTCCGAGCCCTGCGTGCGGCCTGGCCCTGTCAGCAGCC
TGCTGTCCGAGCCTGAAATCGACCACACGAGCCTGAAGGCCGCAGTGGAC
GCCACGGTTGCCTTGCTGGAAAAATCGGCCAGCCCCGTCATGCTGCTGGG
CAGCAAGCTGCGGGCCGCCAACGCACTGGCCGCAACCGAAACGCTGGCAG
ACAAGCTGCMTGCGCGGTGACCATCATGGCGGCCGCGAAAGGCTTTTTCC
CCGAAGACCACGCGGGTTTCCGCGGCCTGTACTGGGGCGAAGTCTCGAAC
CCCGGCGTGCAGGAACTGGTGGAGACCTCCGACGCACTGCTGTGCATCGC
CCCCGTATTCAACGACTATTCAACAGTCGGCTGGTCGGCATGGCCCAAGG
GCCCCAATGTGATTCTGGCTGAGCCCGACCGCGTAACGGTCGATGGCCGC
GCCTATGACGGCTTTACCCTGCGCGCCTTCCTGCAGGCTCTGGCGGAAAA
AGCCCCCGCGCGCCCGGCCTCCGCACAGAAAAGCAGCGTCCCGACGTGCT
CGCTCACCGCGACATCCGATGAAGCCGGTCTGACGAATGACGAAATCGTC
CGTCATATCAACGCCCTGCTGACATCAAACACGACGCTGGTGGCAGAAAC
CGGCGATTCATGGTTCAATGCCATGCGCATGACCCTGCCGCGCGGTGCGC
GCGTGGAACTGGAAATGCAGTGGGGCCATATCGGCTGGTCCGTGCCCTCC
GCCTTCGGCAATGCCATGGGCTCGCAGGACCGCCAGCATGTGGTGATGGT
AGGCGATGGCTCCTTCCAGCTTACCGCGCAGGAAGTGGCTCAGATGGTGC
GCTACGAACTGCCCGTCATTATCTTTCTGATCAACAACCGTGGCTATGTC
ATTGGCATCGCCATTCATGACGGCCCGTACAACTATATCAAGAACTGGGA
TTACGCCGGCCTGATGGAAGTCTTCAACGCCGGAGAAGGCCATGGACTTG
GCCTGAAAGCCACCACCCCGAAGGAACTGACAGAAGCCATCGCCAGGGCA
AAAGCCAATACCCGCGGCCCGACGCTGATCGAATGCCAGATCGACCGCAC
GGACTGCACGGATATGCTGGTTCAATGGGCCGCAAGGTTGCCTCAACCA
ACGCGCGCAAGACCACTCTGGCCCTCGAG
```

The sequence is called seq. no. 28 in the sequence protocol.

SEQ ID NO: 28 is disclosed here by way of example for a DNA which encodes the protein to be modified, according to SEQ ID NO: 29. According to the invention, however, all the other deoxyribonucleic acids which encode the starting protein to be modified can be employed for preparing the enzyme to be modified. The nucleotides encoding these are known to a person skilled in the art.

The associated protein sequence is called SEQ ID NO: 29 in the sequence protocol.

Production of the Variants in the Form of "Whole Cells"

For expression of the enzymes in whole cells on a 1 l scale, cells from the master plate to which glycerol had been added were first transferred with an inoculation loop into 50 ml of LB medium (+100 µg/ml of ampicillin) and the mixture was incubated at 120 rpm and 37° C. in a 250 ml conical flask. After incubation for 16 h, 10 ml of the culture were added to 1 l of autoinduction medium and the mixture was incubated at 90 rpm and 20° C. in a 5 l conical flask for 72 h. The cells were then harvested by centrifugation (4° C., 6,000 rpm, 30 min) and stored at −20° C. until used further.

Autoinduction Medium

| | |
|---|---|
| 12 g/l | peptone |
| 24 g/l | yeast extract |
| 90 mM | potassium phosphate buffer (pH 7.5) |
| 0.5 g/l | glucose |
| 2 g/l | lactose |
| 0.01 g/l | ampicillin |
| 6.3 g/l | glycerol |

Production of the Variants in the Form of Isolated Enzymes 10 g of the cells cultured on a 1 l scale were resuspended on ice with 25 ml of breakdown buffer (50 mM potassium phosphate pH 6.5, 100 µM thiamine diphosphate, 2 mM magnesium sulfate), which was cooled to 4° C. The resuspended cells were then broken down by means of ultrasound (SD14 Sonotrode (Hielscher Ultrasonics GmbH), 4×2 min ultrasound treatment with cooling from ice for 1 min each time). To separate off the cell debris the solution was centrifuged (45 min, 18,000 rpm, 4° C.) and the supernatant (cell extract) was transferred into a new vessel.

For purification of the ApPDC variant by means of immobilized metal ion affinity chromatography and size exclusion chromatography, an ÄKTA™ Purifier from Amersham Bioscience was used in order to detect inter alia the protein UV absorption (280 nm) and the electrical conductivity and to adjust the flow rate. For purification, the cell extract prepared (~25 ml) was applied with a flow rate of 3 ml/min on to a column with a volume of 60 ml of Ni-NTA-Superflow (Qiagen N.V.), which was equilibrated beforehand with 180 ml of the application buffer. Thereafter, the column was flushed further with application buffer in a flow rate of 5 ml/min in order to remove proteins which do not bind or bind very weakly to the column material. After the UV absorption (280 nm) had reached a stable base line again, a wash buffer (50 mM potassium phosphate pH 6.5, 100 µM thiamine diphosphate, 2 mM magnesium sulfate, 50 mM imidazole) was used with a flow rate of 5 ml/min for elution of proteins which bind weakly to the column material. After a renewed stable UV absorption (280 nm) an elution buffer (50 mM potassium phosphate pH 6.5, 100 µM thiamine diphosphate, 2 mM magnesium sulfate, 250 mM imidazole) was used with a flow rate of 5 ml/min for elution of the target protein.

The eluate of the IMAC was applied for rebuffering with a flow rate of 10 ml/min to a size exclusion chromatography column (1 l column volume, Sephadex-G25, GE-Healthcare), which was flushed beforehand with 2 l of rebuffering buffer (10 mM potassium phosphate pH 6.5, 100 µM thiamine diphosphate, 2 mM magnesium sulfate). The fractions with increased UV absorption (280 nm) were combined and frozen in a crystallizing dish (−20° C.). For freeze drying a reduced pressure of 0.22 mbar was applied to the frozen protein solution for 3 days. The buffer formed had a protein content of 20%. The purity (content of the target protein with respect to foreign proteins) was >90%.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A lyase, comprising
an amino acid sequence comprising SEQ ID NO: 1, 3, 9 or 21.

2. A method for producing (S)-phenylacetylcarbinol, comprising reacting benzaldehyde with pyruvate or with acetaldehyde according to formula (1),

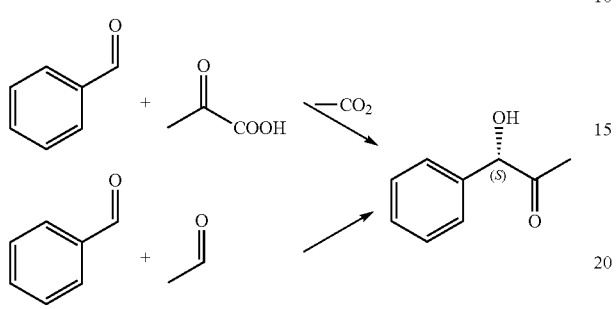

Formula (1)

wherein
the reaction is carried out with the lyase of claim 1.

3. The method of claim 2,
wherein
the reaction is carried out at a pH of 5-9.

4. The method of claim 2,
wherein
HEPES, MOPS, TEA or TRIS-HCl is employed as a buffer.

5. The method of claim 2,
wherein
thiamine phosphate and magnesium sulfate are employed as cofactors.

6. The method of claim 2,
wherein
the reaction is carried out in vitro.

7. The method of claim 6,
wherein
a crude cell extract from a production organism is used.

* * * * *